US008211044B2

(12) United States Patent
Liebowitz

(10) Patent No.: US 8,211,044 B2
(45) Date of Patent: Jul. 3, 2012

(54) MEDICAL DEVICE FOR AN ATHLETE'S DIGITS

(76) Inventor: Tyler Liebowitz, Los Angeles, CA (US)

( * ) Notice: Subject to any disclaimer, the term of this patent is extended or adjusted under 35 U.S.C. 154(b) by 320 days.

(21) Appl. No.: 12/681,528

(22) PCT Filed: Sep. 11, 2007

(86) PCT No.: PCT/US2007/078194
§ 371 (c)(1),
(2), (4) Date: Apr. 2, 2010

(87) PCT Pub. No.: WO2008/033865
PCT Pub. Date: Mar. 20, 2008

(65) Prior Publication Data
US 2010/0234785 A1 Sep. 16, 2010

Related U.S. Application Data

(63) Continuation-in-part of application No. 11/530,756, filed on Sep. 11, 2006, now abandoned.

(51) Int. Cl.
*A61F 5/00* (2006.01)
*A61F 13/00* (2006.01)
(52) U.S. Cl. ............... 602/22; 602/41; 602/42; 602/48; 602/54; 602/58; 607/108; 607/111
(58) Field of Classification Search ............. 602/41–59, 602/2; 2/22, 163; 607/96, 108–112
See application file for complete search history.

(56) References Cited

U.S. PATENT DOCUMENTS

| | | | |
|---|---|---|---|
| 3,980,070 A | 9/1976 | Krupa | |
| 4,366,813 A | 1/1983 | Nelson | |
| 5,431,622 A * | 7/1995 | Pyrozyk et al. | 602/2 |
| D464,140 S * | 10/2002 | Lavin, Jr. | D24/206 |
| 6,514,279 B1 * | 2/2003 | Lavin, Jr. | 607/108 |
| 6,605,751 B1 | 8/2003 | Gibbins et al. | |
| 7,785,359 B2 * | 8/2010 | Latham | 607/111 |
| 2003/0135143 A1 | 7/2003 | Chow | |
| 2004/0138598 A1 | 7/2004 | Kortuem et al. | |
| 2004/0186402 A1 | 9/2004 | Benette | |
| 2005/0103769 A1 | 5/2005 | Marquis | |
| 2005/0203450 A1 | 9/2005 | Shippert | |
| 2006/0004427 A1 * | 1/2006 | Wilson et al. | 607/108 |
| 2009/0165922 A1 * | 7/2009 | Kingsford et al. | 156/66 |

FOREIGN PATENT DOCUMENTS

WO WO2005007303 A1 7/2005

OTHER PUBLICATIONS

Icy Hot Pro-Therapy Knee Brace, Dec. 18, 2007.
Packaging for Icy Hot Pro-Therapy Knee Brace, Dec. 18, 2007.
International Patent Application No. PCT/US2007/078194, International Search Report, dated Apr. 11, 2008.
International Patent Application No. PCT/US2007/078194, International Written Opinion, dated Apr. 11, 2008.
International Patent Application No. PCT/US2007/078194, International Preliminary Report on Patentability, dated Mar. 17, 2009.

* cited by examiner

*Primary Examiner* — Kim M Lewis
(74) *Attorney, Agent, or Firm* — McKee, Voorhees & Sease, P.L.C.

(57) ABSTRACT

A medical device comprising a sheath that fits around at least a portion of the circumference of a finger, optionally comprising a pouch for retaining an insert, for supporting and protecting the finger.

16 Claims, 12 Drawing Sheets

MEDICAL DEVICE FOR AN ATHLETE'S DIGITS

RELATED APPLICATION INFORMATION

This application is the U.S. national stage of International Application No. PCT/US07/78194, filed on Sep. 11, 2007 and titled MEDICAL DEVICE FOR AN ATHLETE'S DIGITS, which claims the benefit of priority from U.S. patent application Ser. No. 11/530,756, filed Sep. 11, 2006 and titled MEDICAL DEVICE FOR AN ATHLETE'S DIGITS. The disclosures of the foregoing applications are incorporated herein by reference in their entirety.

BACKGROUND

This disclosure relates to medical devices for the digits of athletes.

Football, basketball, volleyball, rugby, water polo, soccer, hockey, baseball, softball, golf, tennis, racquetball, table tennis, power lifting, boxing, swimming, polo, lacrosse, gymnastics, track and field and other sports are widely played by many people. Because of the physical nature of sports, finger and toe injuries are common. Toes can be similarly injured, though the treatment options are typically more limited.

Figure 1:
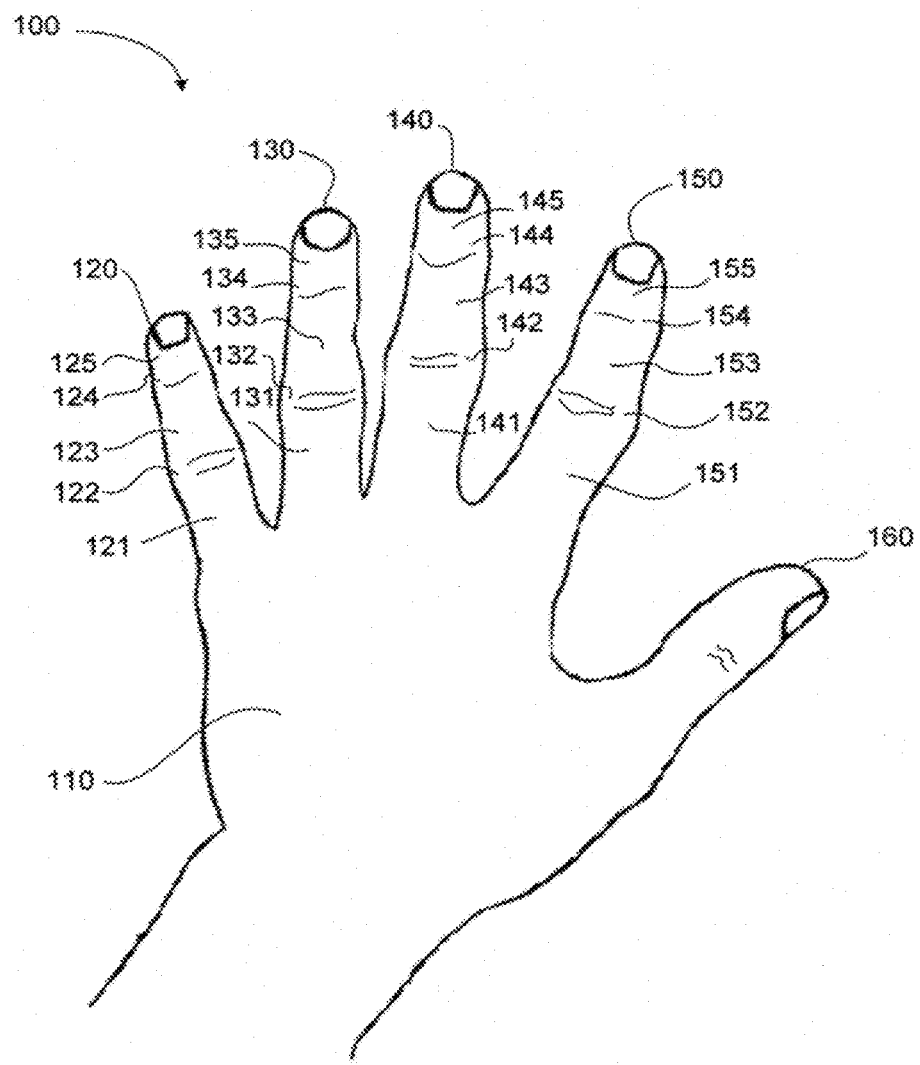

Most people have fifteen finger bones in each hand. Referring to FIG. 1, there is shown the back 110 of a hand 100 of a typical person. The hand 100 includes a pinky finger 120, a ring finger 130, a middle finger 140, a pointer finger 150 and a thumb 160. In turn, the pinky finger 120, ring finger 130, middle finger 140 and pointer finger 150 respectively have a first digit (or phalange) 121, 131, 141, 151, a first knuckle (or joint) 122, 132, 142, 152, a second digit 123, 133, 143, 153, a second knuckle 124, 134, 144, 154 and a third digit 125, 135, 145, 155.

Each of the bones (not shown) within the fingers 120, 130, 140, 150 are connected at the knuckles 122, 132, 142, 152, 124, 134, 144, 154 with ligaments (not shown). Knuckles 122, 132, 142, 152, 124, 134, 144, 154 are susceptible to sprains, strains, dislocations and ligament tears while playing sports.

The term jammed finger refers to an injured finger, due to injuries such as compression, a sprain, a strain, or dislocation of one or more of the joints. Jamming can result following impact with an opponent or teammate, sudden contact with a ball, a fall, or any sudden stretching of a finger 120, 130, 140, 150. Falls onto hard, unyielding surfaces (for example, a basketball floor) can result in jams. It is also common for ligaments to tear near the joints when joints 122, 132, 142, 152, 124, 134, 144, 154 become dislocated. Common treatments for a jammed finger include taping an injured finger to an adjacent finger or splinting a finger.

SUMMARY

In one aspect, the present invention relates to a medical device comprising tape having a first side with an adhesive surface and a second side that has a frictional element or a plurality of frictional elements. The frictional elements, which can be dots, can be arranged on a first side of a finger and not on a second side of the finger when the tape is wrapped around the finger, and/or can be arranged based on the surface of a ball such as a basketball. The first side of the tape can also have a hook fastener.

In another aspect, the present invention relates to a medical device comprising a sheath adapted to fit around at least a portion of a finger and be magnetically attachable and detachable to adjacent sheaths. The sheath can have an outer surface including depressions that are adapted to be fastened with a protrusion, and can have sufficient rigidity to not bend about a knuckle of a finger when a person flexes the finger about the knuckle. In one preferred embodiment, the sheath includes a ferrous material adapted to oxidize and thereby generate heat. The sheath can also include a metal fiber loaded polymer, and/or an anti-bacterial agent.

In yet another aspect, the present invention relates to a medical device comprising a cylindrical body having a geometry for fitting around at least a portion of a finger and an attachment device selected from the group consisting of a tongue and a band, where the attachment device is integral to the cylindrical geometry and is attached to a cylindrical body of another medical device. In this aspect of the invention, the cylindrical body can have an outer surface including frictional elements, e.g. arranged based on the surface of a football. The cylindrical body can also include holes along a side of the cylindrical body and be adapted to be fastened to protrusions of another medical device via the holes. Preferably, the cylindrical body has sufficient rigidity to not bend about a knuckle of a finger when a person flexes the finger about the knuckle. The body can comprise an anti-fungal agent, and the attachment device can be an elastic band.

In further aspect, the present invention relates to sheath for a digit of a hand or foot which comprises a cylindrical body having a geometry for fitting around at least a portion of the digit, a pouch on the top side of the cylindrical body, and an insert sized to be placed through the opening of the pouch and retained in the pouch, wherein the insert provides additional rigidity to the sheath. The insert can comprise materials which retain heat or cold, or which release heat or cold when activated. The opening is preferably removably secured in a closed position by fasteners, such as hook and loop fasteners, in order to better retain an insert. The top side of the pouch and/or the sheath are also preferably formed from insulating materials.

Another aspect of the present invention comprises a medical treatment that involves wrapping a first piece of an elastic tape around a circumference of at least two adjacent digits and a knuckle between the at least two adjacent digits of a first finger, and wrapping a second piece of the elastic tape around a circumference of a second finger, the second finger being adjacent to the first finger. This medical treatment can make use of elastic tape that includes a magnetic material. The treatment can also further comprise securing the first piece of tape to the second piece by attaching a backing across the first surface of both the first piece and the second piece, wherein the backing is disposed proximate a back of the first finger and a back of the second finger.

DRAWINGS

Figure 2:
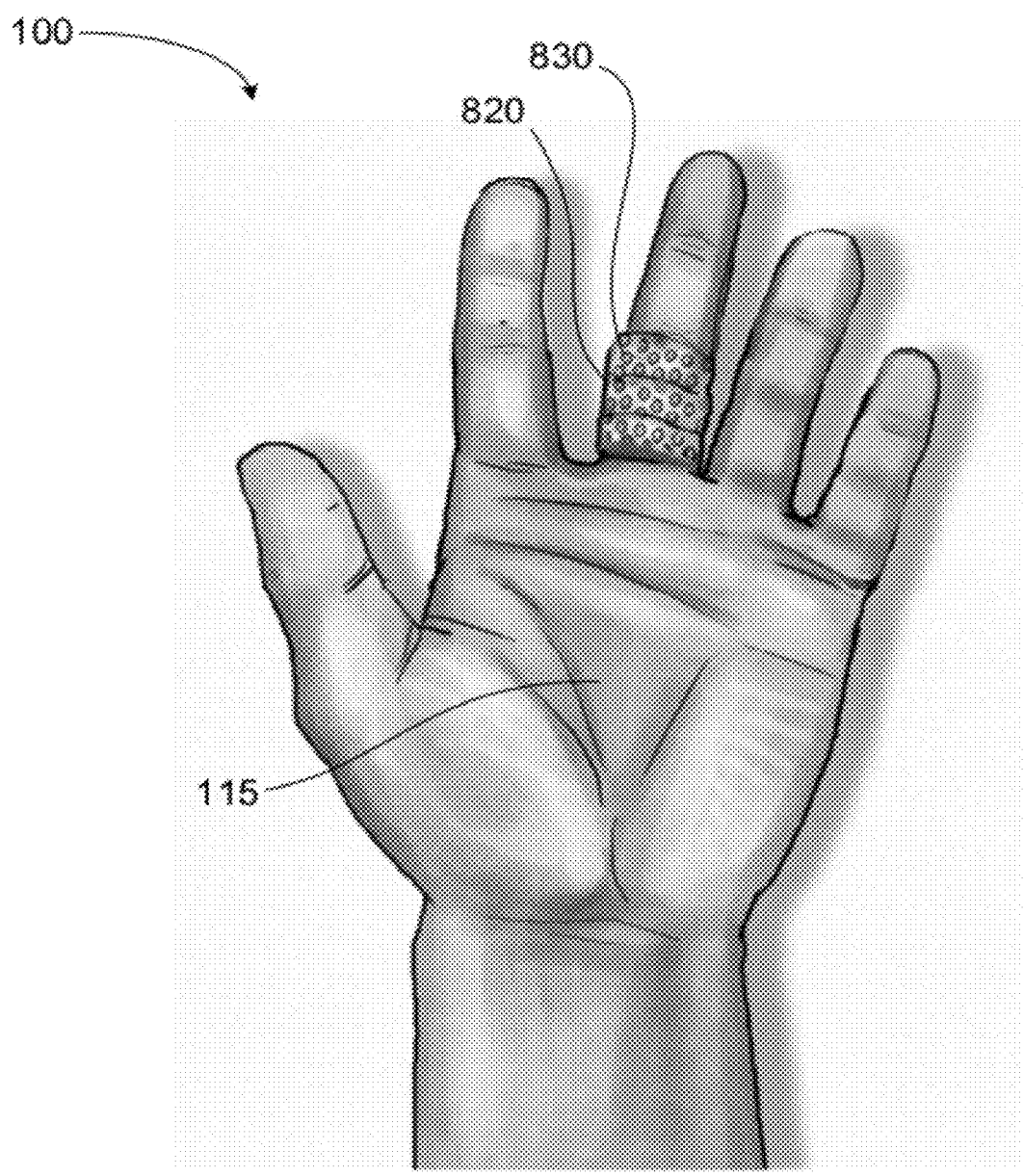
Figure 3:
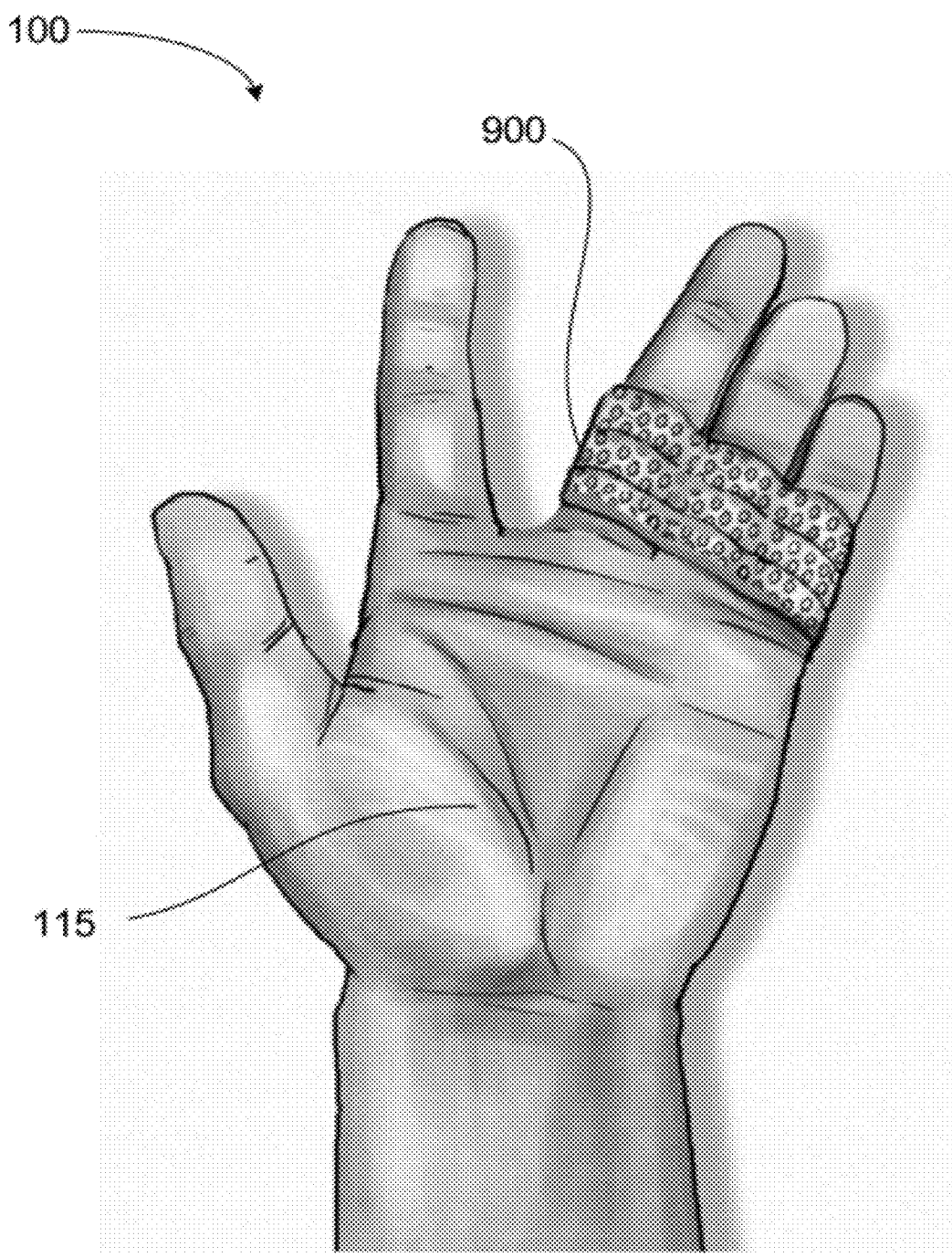
Figure 4:
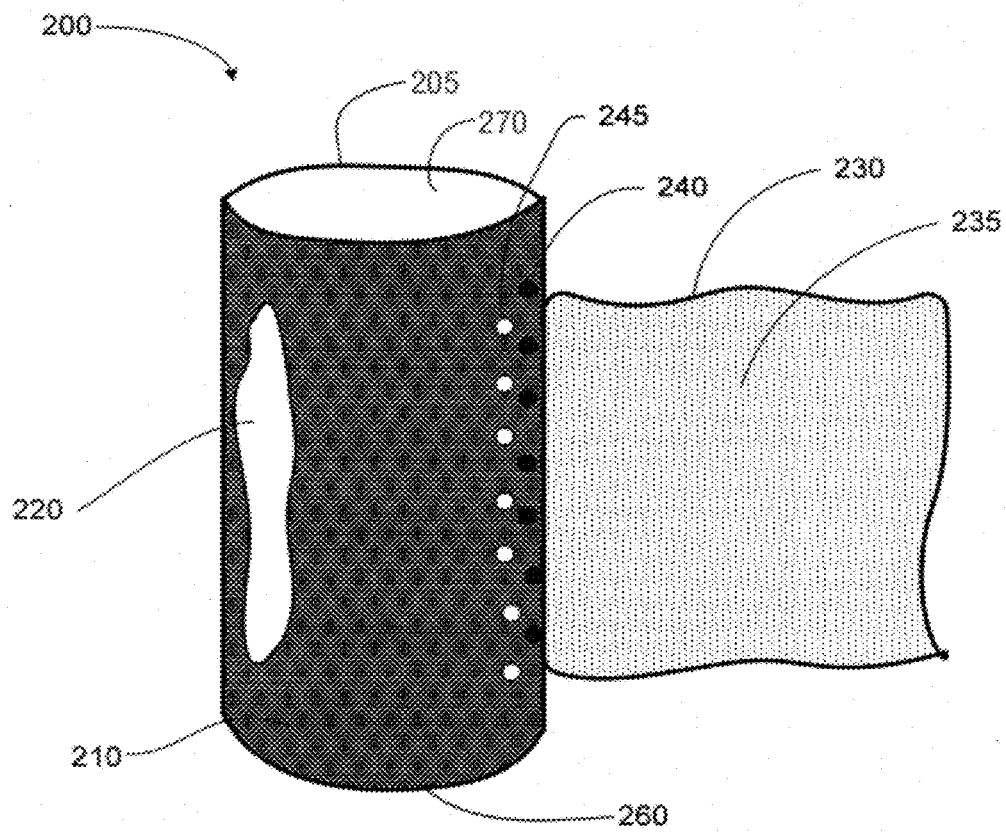
Figure 5:
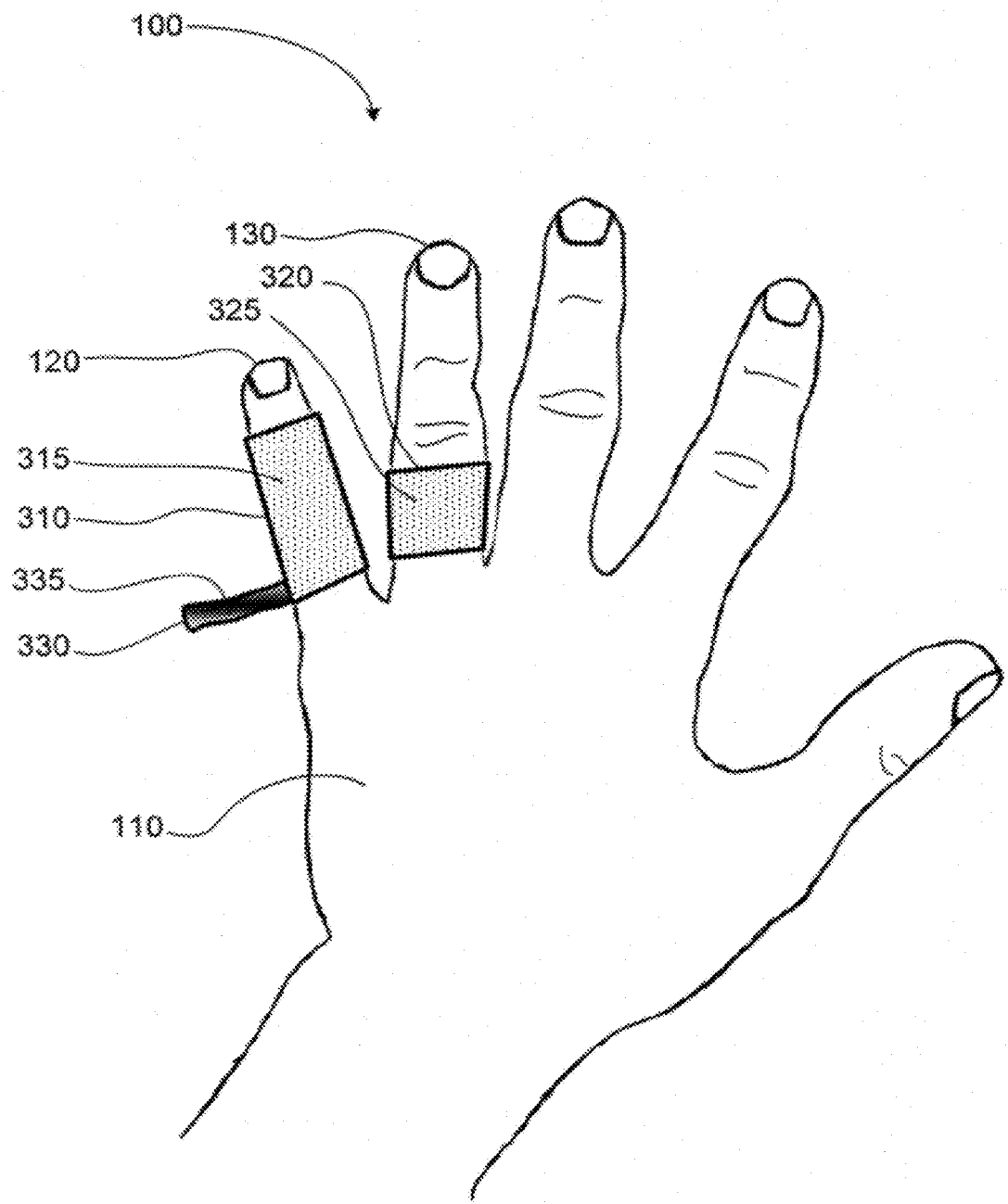
Figure 6:
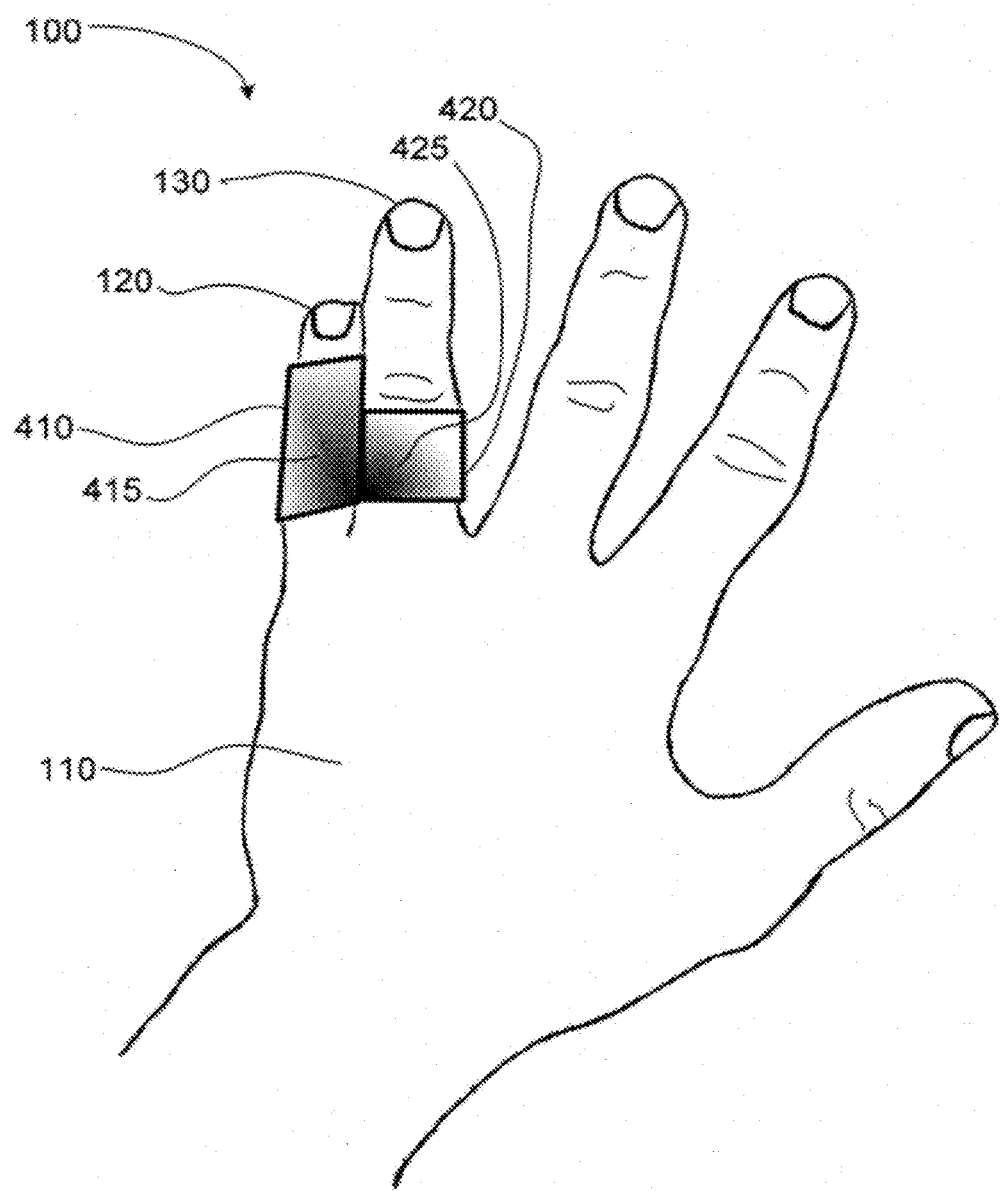
Figure 7:
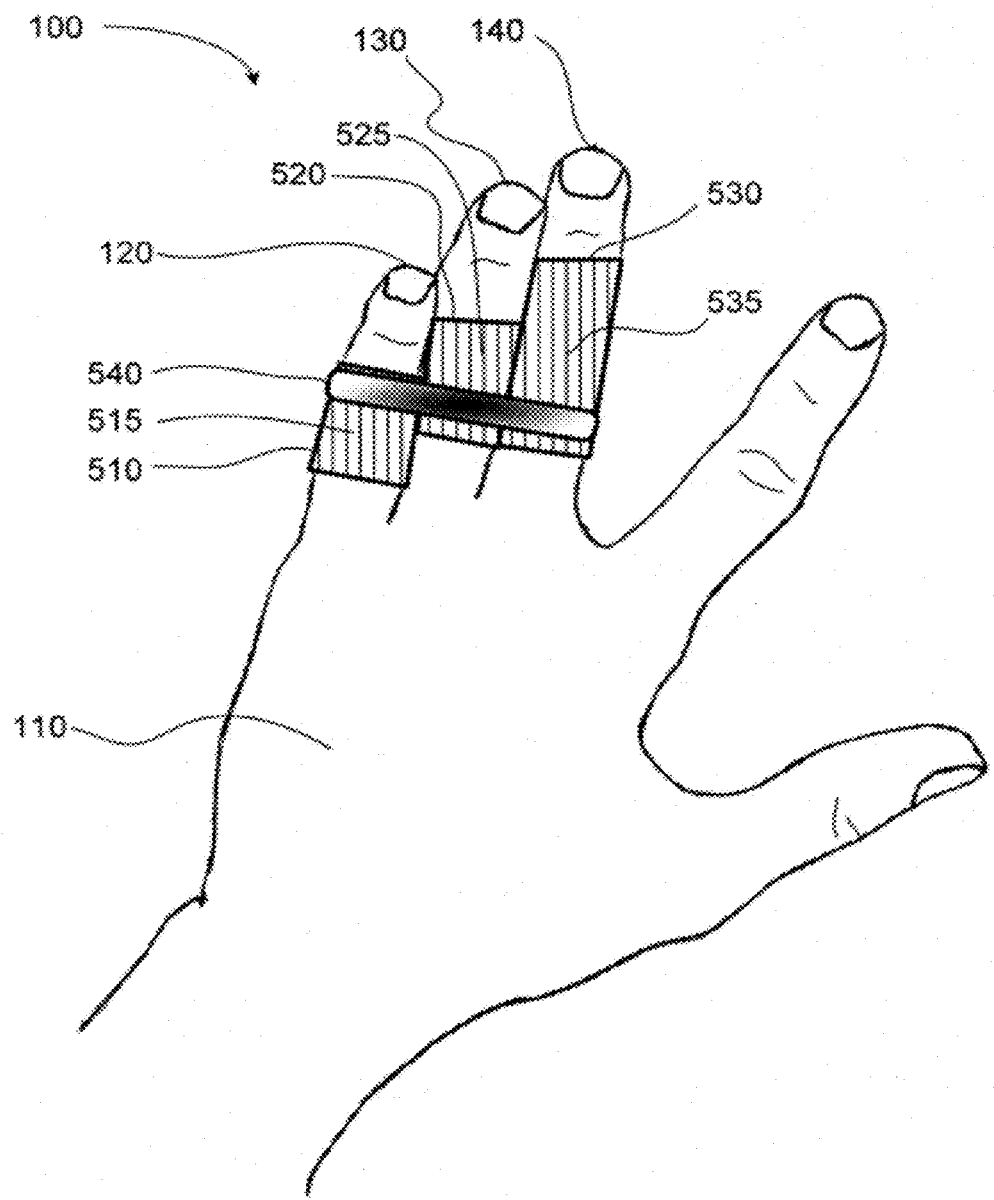
Figure 8:
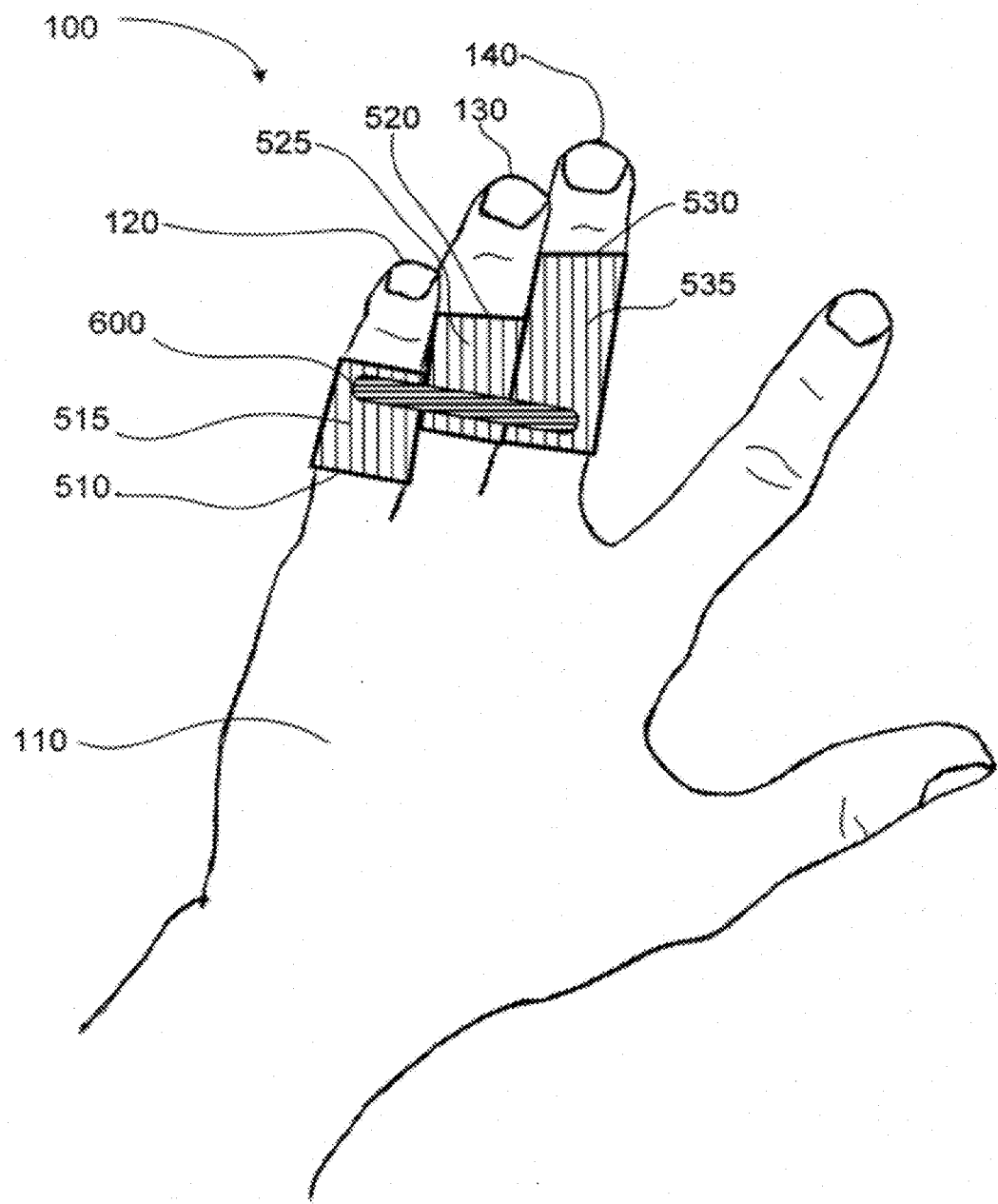
Figure 9:
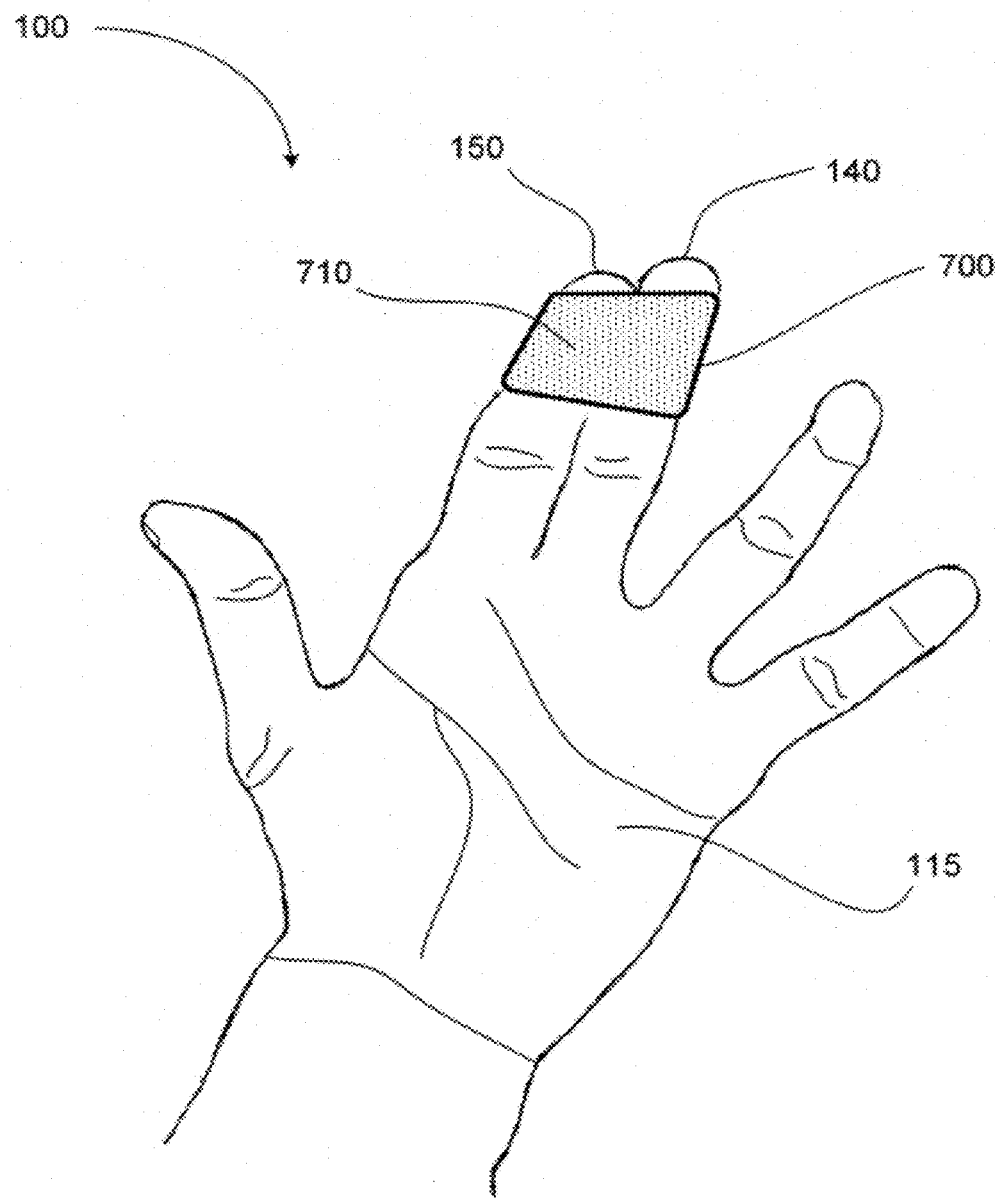
Figure 10:
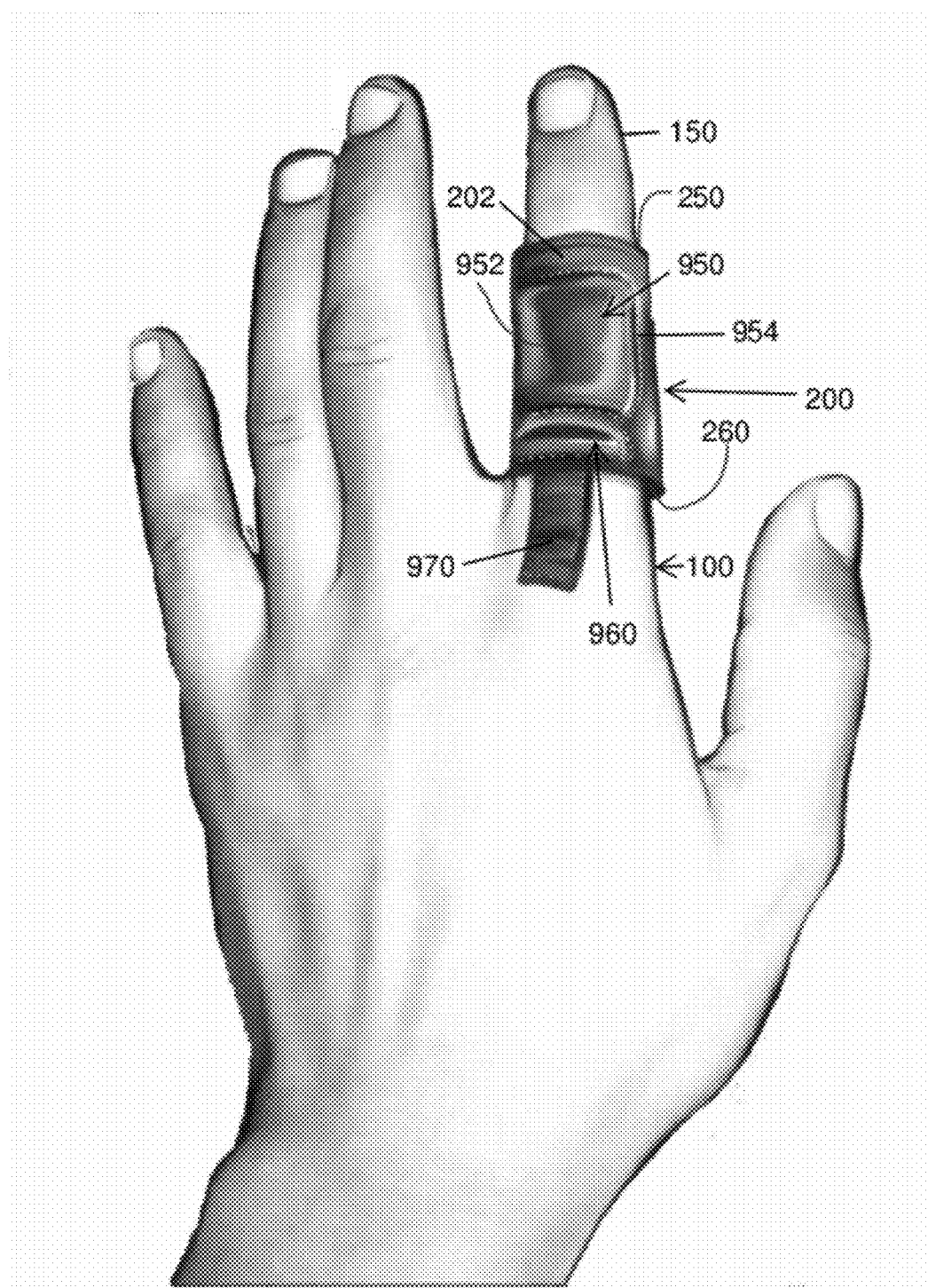
Figure 11:
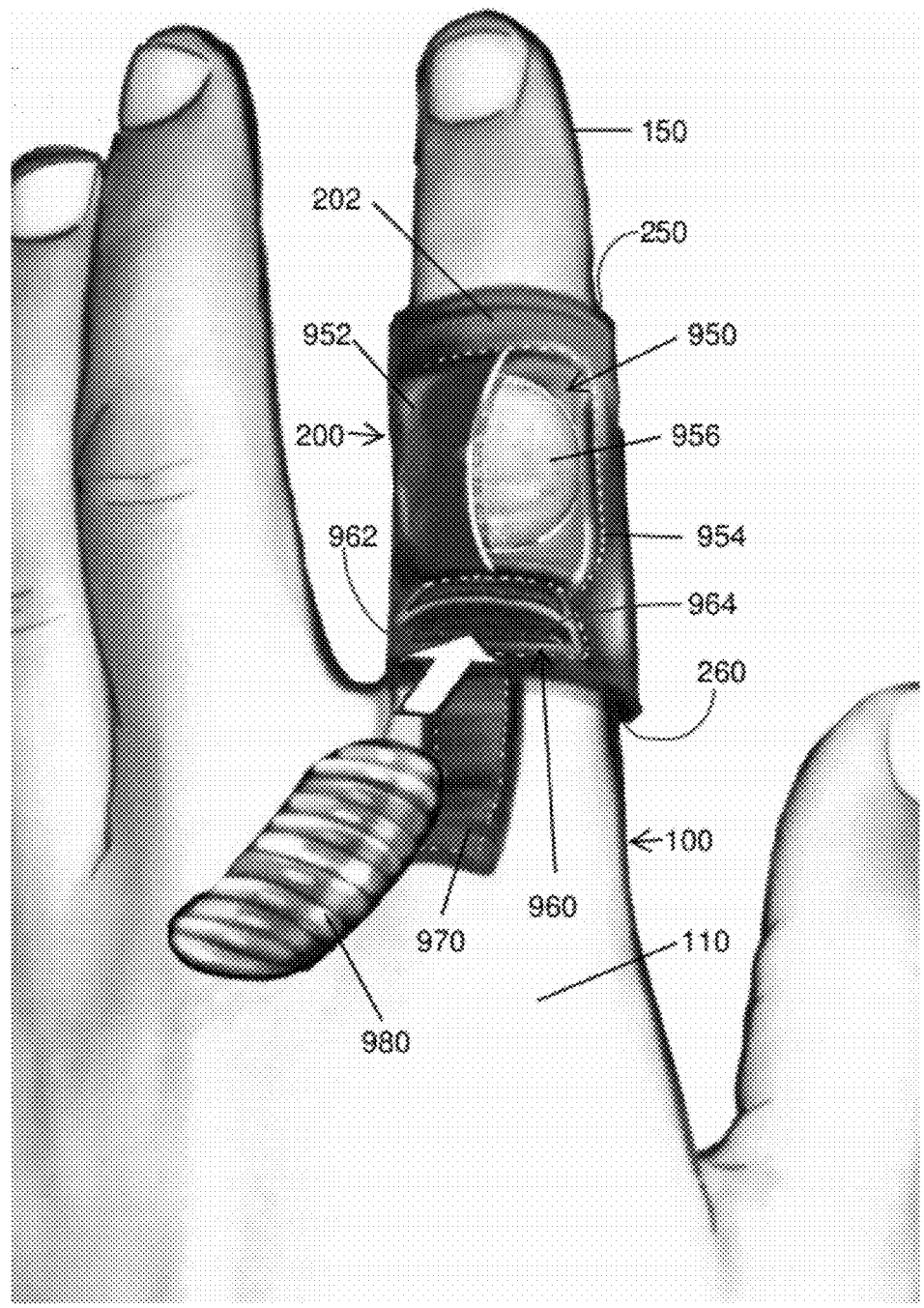

FIG. 1 is a plan view of a back of a hand.
FIG. 2 is a plan view of a palm of a hand with a sheath.
FIG. 3 is a plan view of a palm of a hand with a sheath.
FIG. 4 is a plan view of a sheath.
FIG. 5 is a plan view of a back of a hand with a sheath.
FIG. 6 is a plan view of a back of a hand with a sheath.
FIG. 7 is a plan view of a back of a hand with a sheath.
FIG. 8 is a plan view of a back of a hand with a sheath.
FIG. 9 is a plan view of a palm of a hand with a sheath.
FIG. 10 is a perspective view of a back of a hand having a finger partially covered by a sheath that incorporates an insert.
FIG. 11 is a partial cut-away view of the sheath of FIG. 10.

Figure 12:
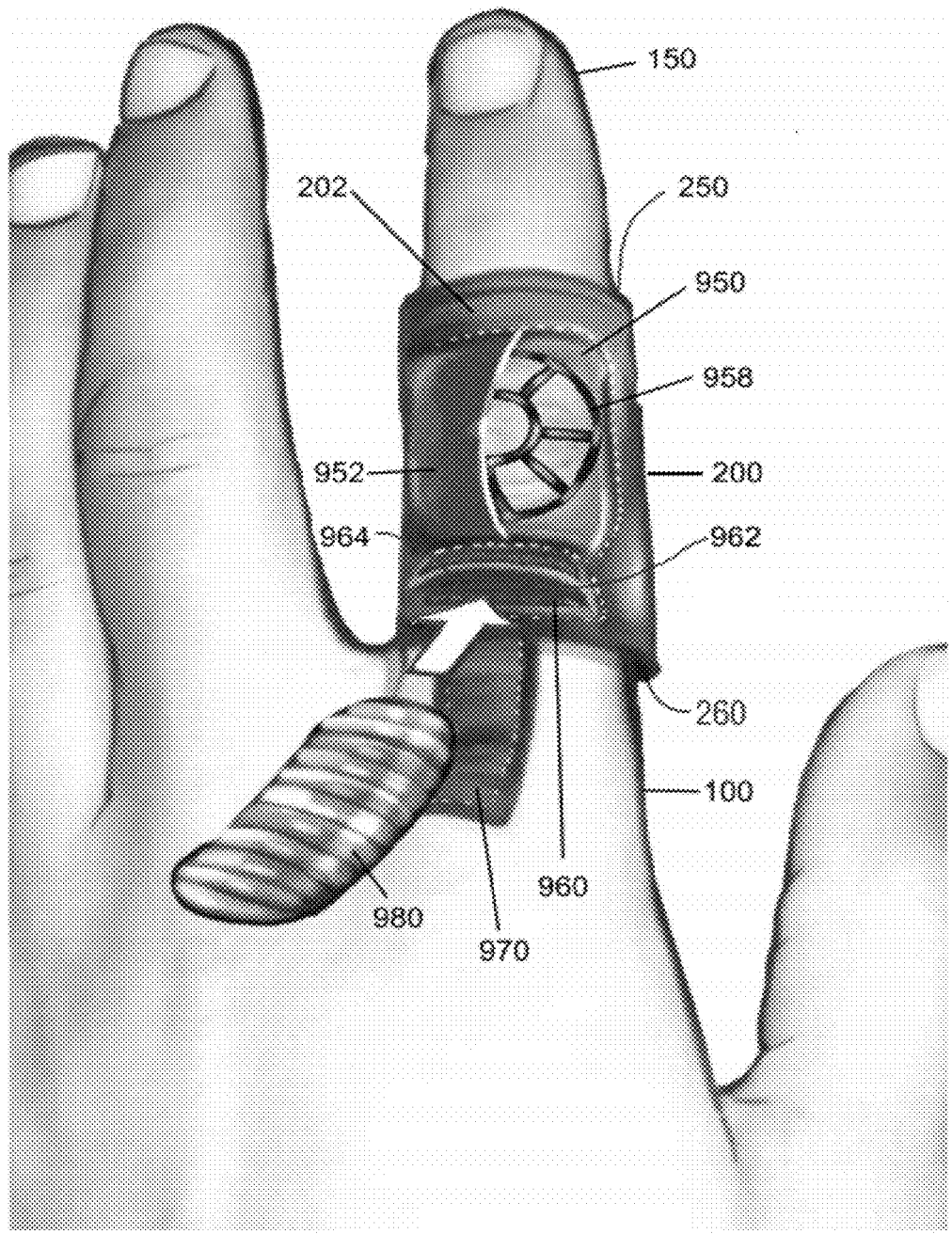

FIG. 12 is a partial cut-away view of an alternative embodiment of the sheath of FIG. 10.

All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by their intended use.

DESCRIPTION

Definitions

As used herein, the following terms and variations thereof have the meanings given below, unless a different meaning is clearly intended by the context in which such term is used.

"Digit" means a finger or toe.

"Plurality" means two or more.

A "set" of items can include one or more of such items.

"Sheath" means a device which at least partially covers and/or supports a digit of a warm blooded vertebrate, in particular a human. Sheaths can have the geometry of a hollow cylinder such as a sleeve, with either open ends or one open end and one closed end, or can comprise other geometries.

The terms "comprising", "including", "carrying", "having", "containing", "involving", and the like are to be understood to be open-ended, i.e., to mean including but not limited to, and are not intended to exclude other additives, components, integers or steps. Only the transitional phrases "consisting of" and "consisting essentially of", respectively, are closed or semi-closed transitional phrases, with respect to claims.

The terms "a," "an," and "the" and similar referents used herein are to be construed to cover both the singular and the plural unless their usage in context indicates otherwise. In addition, the term "and/or" means that the listed items are alternatives, but the alternatives also include any combination of the listed items.

Sheath Embodiments

Referring now to FIG. 2, there is shown a plan view of the palm 115 of a hand 100 and a sheath 820. As the most common finger injured in physical sports is the middle finger 140, the sheath 820 is shown disposed around a circumference of the first digit, first knuckle and the second digit of the middle finger 140. The sheath 820 can have the shape of a thimble, a cylinder, a mitt or other geometry.

The sheath 820 can be utilized as a medical device in a variety of sports. The sheath 820 can provide support to one or more digits and/or one or more knuckles during physical activities. By providing support and rigidity to one or more fingers, the sheath 820 can protect a person's finger from further injury.

The sheath 820 can be formed of a flexible sheet of material, for example, spandex. Spandex is lightweight, durable, soft smooth, supple, and resistant to body oils, perspiration, lotions, and detergents. Moreover, spandex has sufficient flexibility to take the form of a finger when stretched. Because spandex is not very strong, the sheath 820 can be formed by wrapping several layers around the middle finger 820. Additionally, the density of the spandex can be customized to provide a stiffness that prevents the first knuckle from bending. Thus, the spandex can be manufactured such that only a single wrap or layer can be needed to provide desired stiffness to at least partially immobilize a portion of a finger.

Additional materials can be selected based on one or more of density, rigidity and modulus of elasticity. For example, the sheath 820 can include leather, vinyl, cotton, neoprene or other material.

Because people have different size fingers, the sheath 820 can be customized for each person. An example of customizing the sheath 820 is manufacturing the sheath according to ring sizes. Another example of customizing the sheath 820 is providing the sheath 820 in the form of a two sided tape. The term tape refers to a rolled up strip of long, thin anti narrow material. One side of the tape can include an adhesive or fastener, such as a hook and look type fastener. The other side of the tape can include frictional elements 830, disposed on the outside of the middle finger 140, analogous to the features of one or more of a football, a basketball, a volleyball, a rugby ball, a water polo ball, a soccer ball or other sporting device. In order to fully customize the sheath 820, the frictional elements 830 can be spaced along the sheath 820 such that one side of the finger includes frictional elements 830 and the other side of the sheath 820 provides a surface for attachment.

Examples of frictional elements include integrated bumps, dots, ridges, irregularities, granular elements to match a sporting good, and other elements. The frictional elements 830 can be incorporated into the sheath 820 during manufacturing or added manually by an athlete. If the sheath 820 has a relatively high coefficient of friction, then an athlete can grip a ball, a stick, a person, or another object with greater ease than with bare fingers. For example, the frictional surface can include small bumps, hooks, protrusions, suction cups or other features that provide for high friction. Each frictional element can 830 be sized, shaped, positioned and characterized (e.g. its stickiness) to complement the object to be controlled. For example, an array of dots can be used as in U.S. Pat. No. 5,500,956, the disclosure of which is incorporated herein by reference, particularly the disclosures regarding frictional elements 830 and gloves as they can be combined with or used in the medical devices disclosed herein.

Referring now to FIG. 3, there is shown a plan view of the palm 115 of a hand 100 and a sheath 900. As shown, the sheath 900 is formed of a two sided tape wrapped around the pinky finger 120, the ring finger 130 and the middle finger 140. The sheath 900 can be wrapped tightly around the finger 120, 130, 140 in order to bind an injured finger to one or more adjacent fingers. As shown, the ring finger 130 is bound to both the middle finger 140 and the pinky finger 120. Because the ring finger 130 can be generally immobilized by the use of the sheath 900 the ring finger 130 can be protected from further injury.

Referring now to FIG. 4 there is shown a plan view of a sheath 200. The sheath 200 can include a tongue 230 and a body 205. The body 205 can include an outer surface 210, an inner surface 270, an opening 250 disposed at the top end of the body 205, an opening 260 disposed at the bottom end of the body 205, an aperture 220, a depression 245 and a protrusion 240.

The term tongue refers to a projecting section of material which extends from a body. The term body refers to the main or structural portion of a device. The term aperture refers to an opening or open space, such as a hole, gap, cleft, chasm or slit.

The sheath 200 can be manufactured as a unitary device, for example via injection molding, extrusion, weaving, stitching or other process. In turn, the sheath 200 can be adapted to fit a single finger or multiple fingers (as shown in the plan view of a hand 100 in FIG. 9). The sheath 200 can provide support among adjacent fingers. The sheath 200 can be permanently or non-permanently attached to, integrated with, or installed around a glove covering all or other parts of the hand (not shown). As shown in the plan view of a hand 100 in FIG. 5, a first sheath 310 on a pinky finger 120 can be adapted to be repeatedly attached and detached from a second sheath 320 that fits on a ring finger 130.

The characteristics of the sheath 200 can be selected based upon the object to be gripped, and how the fingers are to move. Such objects include basketballs, footballs, baseballs, rugby balls, baseball bats, hockey sticks, golf clubs, tennis racquets and table tennis paddles. For example, in sports which include bats or sticks, at least one knuckle can need to bend in order to control the sporting device whereas the other knuckle can be immobilized and protected.

The strength and weight of the sheath 200 can be determined based on the material that it is manufactured from. Appropriate materials include a plastic, a woven fabric, an elastomer, a rubber, a paper based material, a metal, or combinations of materials. The sheath 200 can include a fabric soaked in a resin, which, when removed from a hermetically sealed package and unraveled onto a finger, cures into a firm covering, such as a mold or cast. The sheath 200 can be an elastomer, such as latex, that unravels onto a plurality of fingers.

Examples of polymers include synthetic resins and organic resins. Organic resins can be thermoplastic, which can aid in the spinning, crimping, shaping and bonding of component sections by thermal processes. Examples of organic resins include hydrocarbon resins such as vinyl, polyvinyl chloride (PVC), polyethylene, polyamides, polyesters, polypropylene or other material. Polymers are inexpensive to manufacture and therefore can be produced for one time usage.

The sheath 200 can be woven from a soft fabric, such as cotton, but can also have some sections which are firm. Stiffness can be varied by section by manufacturing a material which has a greater thickness in a given section or a greater density in a given section. For example, the sheath 200 can include a dense spandex for covering a knuckle, and a less dense cotton to cover the balance of a finger. Thus, the knuckle can be immobilized whereas the balance of the finger is aesthetically dressed. For some professional athletes, a custom device can be produced in order to last several games.

Additionally, to provide support to an athlete's injured finger, a section of the sheath 200 associated with an injured knuckle or digit of the injured finger can include a support, such as one or more hard plastic or metal strips or rods (not shown). The support can be selectively attached to the sheath 200 such that an injured athlete can add additional support as needed.

The body 205 of the sheath 200 can have a geometry that fits over a knuckle and at least a portion of digits of a finger adjacent to the knuckle (not shown). The body 205 can be sufficiently rigid such that an injured knuckle does not flex when a person attempts to flex the finger. Thus, the body 205 can prevent bending about the knuckle of a finger and allow for healing.

The body 205 can define a first opening 260 disposed proximate the bottom of the sheath 200, a second opening 250 disposed proximate the top of the sheath 250 and an aperture 220 disposed along a side of the sheath 200. The aperture 220 can be disposed towards the bottom of the side, the top of the side, the middle of the side, the majority of the length of the side or other configuration. The size of the aperture 220 can be based upon the size of a person's fingertip or other dimension. A person can stretch or slide the first opening 260 over the tip of a finger (not shown) and then down the finger towards the base of a finger. Another embodiment of the body 205 (not shown) does not include the second opening 250 but has a closed tip. This embodiment is suited, e.g., for cold weather sports in order to maintain heat in the finger tip.

The aperture 220 can have geometry and dimensions based the size of a person's fingertip or other dimension. For example, if a person is able to insert a fingertip into the aperture 220, the person can to pull the sheath 200 down across the finger. Additionally, the aperture 220 can provide for breathing of skin and reduction in moisture buildup. An additional embodiment (not shown) includes a plurality of dispersed small apertures to promote cooling and air flow. This embodiment can be selected for sports played in the warm weather and/or when the sheath 200 is worn for a prolonged period of time.

When the sheath 200 is in place on a person's finger, the person's finger tip can be exposed beyond the second opening 250. In some sports, such as basketball, exposed fingers allow the athlete to better control a ball, as an athlete's fingertips are touch sensitive. In this embodiment, the sheath not does not need to extend beyond the midpoint of the second digit of a finger or the first digit of the thumb in order to maintain finger-ball contact.

The outer surface 210 of the sheath 200 can include a high coefficient of friction and/or frictional elements. The outer surface 210 can include an attachment device or fastener to aid in attaching the sheath 200 to another sheath (not shown). Examples of attachment devices include loop fasteners, adhesives, snaps, zippers, slips, combinations herein or other fasteners.

In order to fasten to another sheath (not shown), the tongue 230 can include a first surface 235 which includes hooks that interlock with loops on the another sheath's outer surface (not shown). The first surface of the tongue 235 can include an adhesive or a magnetic material which secures the tongue 235 to the another sheath.

The tongue 230 can have a length that allows the athlete to wrap the tongue 230 around two or more sheaths (not shown) thereby securing the sheath 200 to other sheaths (not shown). An additional embodiment can utilize an elastic band (not shown) integral to the body 205 to wrap around and secure the sheath 200 to adjacent sheaths (not shown).

Attachment features can be disposed along the body 205 and/or the tongue 230. Attachment features can be disposed proximate the adjacent sections of the sheath of one finger to the sheath of the adjacent finger.

As shown in FIG. 4, the protrusion 240 and depression 245 define interlocking members which provide for mechanical fastening between the sheath 200 and an adjacent sheath (not shown). The protrusion 240 can have the shape of a nipple, tab or other shape. The depression 245 can extend at least partially into the body 205 or be a hole in the body 205. The depression 245 and the protrusion 240 can have respective dimensions such that they interlock with a friction fit, an interference fit or other fit. Examples of protrusions and depressions include dimples and holes, snaps, pegs and holes, and other male and female members.

Interference fits are characterized by a diametral interference of approximately 0.001 to 0.002 units per unit of depression diameter. Friction fits are characterized by diametral interference of less than approximately 0.001 to 0.002 units per unit of depression diameter.

In order to maintain an interference fit and/or a friction fit, the protrusion 240 and the depression 245 can be manufactured with a low coefficient of elasticity. In turn, the protrusion and the depression 245 can not easily deform or separate. Hard polymers, dense fabrics, metals and other materials can provide these properties.

The inner surface 270 can include an attachment device. For example, if the body 205 is formed by a material that is able to be rolled, but not bent axially, the body 205 can be formed by a sheet including one or more attachment devices. In fact, the inner surface 270 can include an adhesive to secure the body 205 to a person's finger.

The body 205 can be directionally flexible and/or directionally rigid depending on the type of sport the athlete is playing. For example, in sports like lacrosse or hockey, a person holds a stick with the fingers curved around the stick. If the person's second knuckle is injured, it can be necessary to immobilize the second knuckle, but allow the first knuckle to bend. However, due to swelling, the injured finger can have a swelling about the injury that is up to approximately two times the circumference of the adjacent digit. Therefore, the body 205 can need to stretch axially and radially while being applied to the injured finger and then provide bending rigidity about the injured section. Moreover, based on the sport, the body 205 can be adapted to provide bending rigidity along the whole finger, one portion of the finger, or multiple portions of the finger. When holding a bat or stick, the person can desire a single knuckle maintained in a straight set with the other knuckle having the ability to bend. When playing a game such as basketball, the entire finger can be restrained from bending. The amount of bending and where bending can or can not occur can be determined by a sports physician, a physical therapist, a professional trainer, a nurse, first aid provider, an emergency services provider or other heath care professional.

Directional rigidity can be provided by incorporating axially aligned metal fibers, carbon fibers or other materials in conjunction with a polymer and/or fabric. Such metallic components can allow for magnetic properties. Examples of metallic components include wood, metal or composite wires, rods or strips, metal powder loaded polymers, metal fiber loaded polymers and other components.

Additionally, a customized set of one, two, three, four or five sheaths 200 can be temporarily or permanently fixed to or inside of a baseball glove, a football glove, a golf glove, a soccer goalie glove, a rugby glove, a volleyball glove, a wrestling glove, a weight lifting glove, a track and field glove, a water polo glove, a hockey glove or other glove (not shown).

Physical sports generally result in sweating. Thus, bacteria, mold, fungus and other undesirable microorganisms can attempt to grow on the sheath 200. In order to retard growth of the undesirable microorganisms, the material of which the sheath 200 is manufactured can include or be treated with one or more anti-fungal or anti-bacterial agents.

An example of a chemical that acts both as an anti-bacterial and an anti-fungal agent is an oxy-substituted aromatic arsine such as oxybisphenoxarsine (OBPA). The oxysubstituted aromatic arsine, such as OBPA, is a bacteriostat, disinfectant and fungicide. OBPA prevents the growth of microorganisms when compounded in resins and also acts as a preservative. OBPA can be formulated as an emulsifiable concentrate, pelleted, tableted, soluble concentrate/liquid and ready-to-use liquid. OBPA can be incorporated into a polymer or cloth of which the sheath 200 is formed.

Referring now to FIG. 5, there is shown a plan view of the back 110 of a hand 100. The hand 100 includes a pinky finger 120 and a ring finger 130. Disposed around the pinky finger 120 from a first digit to a third digit is a first sheath 310. Disposed around a circumference of the first digit of the ring finger 130 is a second sheath 320.

The first sheath 310 includes an outer surface 315 and a tongue 330. The tongue 330 includes a first surface 335. The second sheath 320 includes an outer surface 325. The first surface 335 of the tongue 330 can be adapted to secure the first sheath 310 to the second sheath 320. For example, the first surface 335 of the tongue 330 can include an adhesive.

If the first sheath 310 is secured to the second sheath 320, then an injured pinky finger 120 can be immobilized relative the first digit of the ring finger 130. By securing the first sheath 310 to the second sheath 320, additional strength and control can be exercised in various maneuvers. For example, when a basketball athlete attempts to gain control of a basketball via a rebound, if the ball hits a tip of the pinky finger 120, the first sheath 310 and the second sheath 320 can provide strength amongst the pinky finger 120 and the ring finger 130 and distribute the impact among the pinky finger 120 and the ring finger 130 and not further injure the pinky finger 120.

Referring now to FIG. 6, there is shown a plan view of the back 110 of a hand 100. The hand 100 includes a pinky finger 120 and a ring finger 130. A first sheath 410 is disposed around the pinky finger 120 from the first digit to the third digit. A second sheath 420 is disposed around the ring finger 130 about the first digit.

In the embodiment of FIG. 6, the first sheath 410 includes an outer surface 415 which includes a magnetic material and the second sheath 420 includes an outer surface 425 which includes a magnetic material. As shown, the magnetic material of the outer surface 425 of the second sheath 420 magnetically secures to the outer surface 415 of the first sheath 410. Magnetic attachment can be utilized where any additional material or protrusion could improve the player's performance. For example, in baseball, a player throwing a baseball can need sheaths that are thin, fitted specifically to their fingers and do not provide much bulk between the fingers and the ball.

Referring now to FIG. 7, there is shown a plan view of the back 110 of a hand 100. The hand 100 includes a pinky finger 120, a ring finger 130 and a middle finger 140. Disposed around the pinky finger 120 from the first digit to the second digit is a first sheath 510. Disposed around the ring finger 130 from the first digit to the second digit is a second sheath 520. Disposed around the middle finger 140 from the first digit to the second digit is a third sheath 530. The first finger sheath 510, the second finger sheath 520 and the third finger sheath 530 respectively prevent bending of the first knuckle of the pinky finger 120, the ring finger 130 and the middle finger 140.

The first finger sheath 510, the second finger sheath 520 and the third finger sheath 530 can respectively include ridges 515, 525, 535 in the outer surfaces. The first finger sheath 510, the second finger sheath 520 and the third finger sheath 530 can be attached to each other via a band 540. The band 540 can wrap around the finger sheaths 510, 520, 530 and interlock with the ridges 515, 525, 535 in order to prevent the finger sheaths 510, 520, 530 from moving relative to each other. Additionally, the band 540 can be an elastic member to fit tightly around the finger sheaths 510, 520, 530. In turn, the finger sheaths 510, 520, 530 and the band 540 provide protection to the first knuckles of the pinky, ring and middle fingers from jams or other injuries.

Referring now to FIG. 8, there is shown a plan view of the back 110 of a hand 100. The hand 100 includes a pinky finger 120, a ring finger 130 and a middle finger 140. Disposed around the pinky finger 120 from the first digit to the second digit is a first sheath 510. Disposed around the ring finger 130 from the first digit to the second digit is a second sheath 520. Disposed around the middle finger 140 from the first digit to the second digit is a third sheath 530. The first finger sheath 510, the second finger sheath 520 and the third finger sheath 530 respectively prevent bending of the first knuckle of the pinky finger 120, the ring finger 130 and the middle finger 140.

The first finger sheath 510, the second finger sheath 520 and the third finger sheath 530 can respectively include axial depressions 515, 525, 535 in the outer surfaces. The first finger sheath 510, the second finger sheath 520 and the third finger sheath 530 can be attached to each other via a strip 600. The strip 600 can include ridges which interlock with the axial depressions 515, 525, 535 in order to prevent the finger sheaths 510, 520, 530 from moving relative to each other. Moreover, the strip 600 can include an adhesive and/or magnetic material to provide additional binding to the finger sheaths 510, 520, 530 such that the strip 600 is disposed only on the portion of the finger sheaths 510, 520, 530 toward the back 110 of the hand 100. Therefore, the strip 600 need not contact a ball when an athlete handles a ball.

Referring now to FIG. 9, there is shown a plan view of the palm 115 of a hand 110. The hand 100 includes an index finger 150 and a middle finger 140. Disposed around the outside of the index finger 150 and the middle finger 140 from the respective second digit to the respective third digit is a sheath 700. The sheath 700 includes an outer surface 710.

Because the sheath 700 secures the second knuckle of the index finger 150 and the second knuckle of the middle finger 140 relative one another, injury to second knuckles can be prevented. The outer surface 710 can include small suction cups or sticky dots to aid in the handling of a sports ball such as a football. For example, a wide receiver can be able to catch a pass easier with the sheath 700.

Additionally, by securing one or more sheaths to one or more other sheaths in a relatively fixed position, a predetermined angle can be set for optimum performance. For example, if the digits of the fingers are set in a general "C" geometry, an athlete can have an advantage while managing a lacrosse stick (not shown). If the digits of the fingers are set in a general "(" geometry, an athlete can have an advantage while passing a football (not shown).

Additionally, by securing one or more sheaths to one or more other sheaths in a generally planar geometry, a martial arts practitioner can have an advantage when striking an opponent or an object due to the rigidity amongst the sheaths (not shown).

Detachability and re-attachability can also provide other benefits. This includes replacement of worn sheaths. Also, an athlete can change the appearance of their sheath by replacing one or more sheaths with one appearance (e.g., color) with sheaths of a different appearance. Moreover, the sheath can include an appealing fragrance or deodorant which can increase demand among feminine athletes and/or athletes who are offended by the smell of dried sweat.

Another benefit of detachability (and re-attachability) is the ability to conform to varying rules. That is, some rules can allow an open tipped sheath whereas some sports may allow only a closed tipped sheath (not shown). Additionally, some rules may allow for the sheaths to be attached to one another, whereas others may require the sheaths not to attach to one another.

Moreover, rules may permit or prohibit friction enhancing features in varying locations.

The relative position of various parts of the sheath 200 is described based upon the view of FIG. 4. For example, terms such as top, bottom, inner, outer, side, left and right are disclosed. However, the platform sheath 200 can be used in various positions such as upside down or inside out. Thus, some descriptive terms are used in relative terms and not absolute terms.

Although shown implemented with fingers, the apparatus can be implemented with human toes, and/or fingers and toes of warm blooded vertebrate pets.

Sheaths with Inserts

In some situations it can be advantageous to provide warmth to a joint and/or to a digit of an athlete or other individual. For example, a finger can become numbingly cold in cold weather, and use of the finger can become relatively impaired with respect to engaging in a sporting activity. For sports played in cold weather environments, such as skiing, snowboarding, ice hockey, and sometimes football, this is a particular issue.

In other situations, cooling of a joint and/or a digit can be beneficial, for example to reduce swelling and to provide relief from pain and stiffness. Additionally, when injuries first occur in a digit, a health care professional may recommend cooling of the injured area.

In order to provide heating or cooling to a joint and/or to a digit, as appropriate, while maintaining support for the joint and/or digit, the present sheaths 200 can be provided with pouches 950 for retaining a thermal insert 980. Such pouches can be incorporated into any of the foregoing embodiments of the present sheaths 200, and are preferably positioned adjacent to an area, such as a joint, which might benefit from heating or cooling. The pouch 950 can thereby retain a thermal insert 980 adjacent to a joint and/or another portion of a digit of an individual wearing a sheath 200 in order to provide local heating or cooling. Preferably, the insert 980 is retained within a pouch 950 directly over an area in need of heating or cooling, such as a joint.

The insert 980 is also preferably maintained within a pouch 950 in a secure manner, either by means of a friction fit within the pouch 950 (which can be accomplished through the use of an elastic material to form the pouch 950 and/or the remainder of the sheath 200) or through the use of fasteners, such as hook and loop fasteners, which secure the insert 980 within the pouch. Thermal inserts 980 are preferably removably secured within pouches 950 so that an insert 980 which is no longer providing sufficient heating or cooling can be removed from the pouch 950 and replaced with another insert 980 or with the same insert after it has been re-cooled or re-heated (if the design of the insert 980 allows for this). However, in embodiments of the present sheath 200 which are designed to be used only once, an insert can be permanently secured within a pouch 950, such as by being completely stitched within the pouch 950 of a sheath 200.

Heat can be provided by a thermal insert 980 in various ways. In one embodiment, the thermal insert comprises or contains a material which retains heat and then releases it, such as water, in which case the thermal insert 980 is heated prior to insertion into a sheath 200. Alternatively, a thermal insert 980 can comprise a material or materials which generate heat when activated, for example a ferrous or other material that undergoes an exothermic reaction and creates heat when it oxidizes, in which case the thermal insert is generally a single-use item (i.e., it can be used only one-time). The thermal insert in this embodiment can comprise one or more compartments which retain the heat generating materials in an inactivated state until needed. For example, calcium chloride or magnesium sulfate can be maintained in one compartment and water in another, and the contents of one compartment later combined with the other when heat is desired, such as by breaking a seal or other barrier separating these components, which then undergo an exothermic reaction. Alternatively, a miniature heating coil or element powered by a lithium-ion battery or other power source can be embedded in the thermal insert 980 and/or in the material of the sheath 200 and can be activated via a control, such as a pressure switch, in order to provide heat.

Cooling can likewise be provided by a thermal insert 980 in various ways. The thermal insert 980 can comprise a material which can be cooled or frozen prior to use and which then absorbs heat when applied, such as water or a refrigerant gel or liquid. Alternatively, the thermal insert 980 can comprise one or materials which undergo an endothermic reaction when activated, absorbing heat from their surroundings. Such materials can be maintained in separate compartments and later combined when cooling is desired, such as by breaking a seal or other barrier separating these components. For example, water and ammonium nitrate can be maintained in separate compartments and then combined when cooling is needed, at which point these components are placed into contact with each other. Alternatively, ammonium nitrate, sodium acetate trihydrate and an aqueous solution of ethylene glycol can likewise be maintained in separate compartments until cooling is needed. A commercial cold pack comprising materials of this nature is available as Icy Hot® Pro-Therapy™ Instant Cold Packs, made by Chattem, Inc., Chattanooga, Tenn.

In a preferred embodiment, the thermal inserts 980 comprise a rigid or semi-rigid material, in order to facilitate the ease of insertion into a pouch 950. If the covering for the heating or cooling materials of the thermal insert 980 is not formed from a sufficiently rigid material to allow the insert 980 to be placed in the pouch 950 without the aid of a rod or other rigid structure, the covering and thermal material of the thermal insert 980 can be attached to a further more rigid structure. Preferably, the covering of the thermal insert is attached to such a structure only on its sides and/or around its periphery, and the covering of the thermal insert 980 adjacent to the user's skin (once the insert 980 is placed in a pouch 950) is not further covered by an additional structure, so that the structure does not interfere with the transfer of heat or cooling from the insert 980 to the user's skin. The amount of rigidity added by the rigid structure can be varied depending on the amount of rigidity desired by a user or recommended by a medical practitioner.

In another embodiment, non-thermal material inserts can be placed in the pouch 950 in order to vary the amount of rigidity (resistance to flexing/bending) of the present sheath 200. Different materials and/or thicknesses of material can be used as such material inserts, with more material inserted into the pouch 950 generally resulting in greater rigidity. Preferably, such material inserts are used in embodiments in which a pouch 950 is positioned across the two sides of a joint, as shown in FIGS. 10-12, and the inserts are elongated in shape so as to extend across the joint. When inserts extend across a joint in this way, in particular when positioned on the top side 202 of the sheath 200 so as to overlay the top side of a joint, the rigidity added to the sheath 200 by the insert is increased. Inserts used to increase the rigidity of the present sheath 200 can be used with the embodiments of the present sheath 200 in the same way as the thermal inserts 980 described herein.

In a further embodiment, an insert comprising a topical medication or other topical ointment can be inserted into a pouch 950 of the present sheath 200. In this embodiment, such a topical delivery insert can comprise a medicated foam pad which carries such a topical ointment, in which case the pouch 950 is preferably either open below the insert or comprises a material having openings between the insert and the skin of a user, such as the mesh material illustrated in FIG. 11. The material carried by an insert in this embodiment can be, for example, a topical analgesic, such as trolamine salicylate (found in ASPERCREME topical analgesic, available from Chattem, Inc., Chattanooga, Tenn.) or the composition sold as ICY HOT comprising methyl salicylate and menthol (also available from Chattem, Inc.). Topical delivery inserts can be used in the present sheath embodiments in the same way as the thermal inserts 980 described herein.

In embodiments comprising a pouch 950 for use with thermal inserts 980, the sheath 200 is preferably formed at least in part from a material with insulating characteristics. Preferably, the portion of the sheath 200 overlying the area of a digit where cooling or heating is desired comprises such an insulating material. A preferred material is NEOPRENE polychloroprene (available from DuPont Performance Elastomers, LLC, Wilmington, Del.), due both to its insulating characteristics and to its elasticity, as it has a modulus of elasticity which permits the bending of a digit between an extended state and a retracted state (i.e. when a finger curls, as when forming a fist). In the embodiment of a sheath 200 shown in FIGS. 10-12, for example, the upper surface 952 of the pouch 950 preferably comprises NEOPRENE polychloroprene in order to lessen the loss of heating or cooling to the atmosphere outside the sheath 200 and to allow bending of the joint 152 beneath the pouch 950. More preferably, the remainder of the top side 202 of the sheath 200 (i.e. the portion which covers the back of a digit, opposite the palm side) and/or of the entire sheath is made from this material. Insulating materials preferably provide insulation equivalent to that provided by NEOPRENE polychloroprene which is at least 1 millimeter thick, and preferably at least 4 millimeters thick.

An embodiment of a sheath 200 comprising a pouch 950 is shown in FIG. 10. In the illustrated embodiment, the pouch 950 covers a portion of the top side 202 of the sheath 200, in particular the portion of the sheath 200 overlying joint 152. While a single pouch 950 is illustrated in this figure, it is to be understood that multiple pouches can be used in other embodiments. Pouches 950 which extend around the circumference of a digit can also be used. Likewise, pouches 950 can be incorporated into other embodiments and geometries of a sheath 200, such as a sheath 200 having a closed tip in place of the opening 250 in the sheath 200 illustrated in FIG. 10.

In the embodiment of FIG. 10, the pouch 950 is formed by stitching 954 around a portion of the periphery of the pouch 950, which is located in a portion of the top side 202 of the sheath 200. The upper surface 952 of the pouch 950 in this embodiment thus comprises a portion of the top side 202 of the sheath 200. In these illustrated embodiments, a flap 970 is attached to the lower end of the sheath 200 in order to aid in putting on and/or removing the sheath 200 from a digit (index finger 150 in FIGS. 10-12).

A pouch opening 960 is provided to allow for the insertion and removal of thermal inserts 980, as shown in FIGS. 11 and 12. Preferably, the pouch opening 260 comprises an top inner surface 962 and a bottom inner surface 964, and these surfaces are provided with a fastener system which allows the pouch opening 960 to be removably secured. Preferably the top inner surface 962 and bottom inner surface 964 comprise hook and loop fasteners. The use of a sufficiently elastic material to form the pouch 950 and/or other portions of the top side of the sheath 200 may make it unnecessary to provide a fastening system for the pouch opening 260 if inserts 980 are suitably retained in the pouch 950 without such a fastening system.

FIGS. 11 and 12 are partial cut-away views of the present embodiment of a sheath 200 which show the interior of the pouch 950. In the embodiment of FIG. 11, a mesh material 956 attached to the interior of the sheath 200 is provided. The mesh material 956 is positioned underneath the pouch 950, and acts as a barrier between the upper portion of the pouch 950 and the skin of an individual wearing the sheath. The mesh material 956, which can also comprise other material with or without openings, helps to retain the insert within the pouch 950, and can in some cases modulate the rate at which heating or cooling is transferred between a thermal insert 980 and the skin of a user. This can be advantageous in situations in which the thermal insert 980 may initially be hotter or cooler than desired when first activated.

FIG. 12 illustrates a pouch 950 having a rigid support 958 on the interior of the pouch 950. The rigid support 958 defines a space on the interior of the pouch 950, and can help to prevent inadvertent activation of a single-use thermal insert 980 that's been inserted into the pouch 950. The rigid support 958 can be formed, e.g., of any suitable rigid material, such as PVC plastic.

In use, an insert 980 is placed in the pouch 950 by opening the pouch opening 960 and placing the insert 980 through this opening 980. If the insert 980 is a single-use thermal insert, it can be activated either prior to insertion into the pouch 950 or afterward. If the insert 980 is built into the pouch 950, it would be activated when needed. Preferably, such single-use thermal inserts are activated through bending or other flexing of the insert 980, so that when used in a pouch 950 adjacent a joint, the thermal insert 980 will be activated through the flexing or retraction of the finger on which the sheath 200 is being worn.

In one embodiment, the present sheaths 200 comprising pouches 950 can be designed to be worn over a glove on the fingers of an individual, in which case such a glove preferably includes an opening (optionally covered by a flap or other covering which can be removably secured) over which the sheath 200, and in particular a pouch 950 of the sheath 200, can be positioned. Preferably such a glove comprises a flapped opening over or near a joint such as a knuckle in order to provide heating and/or cooling to the joint.

It is to be understood that the embodiments of the present sheath 200 incorporating pouches 950 described above are not limiting, and that such pouches and the inserts which are useful with these pouches can be incorporated into any of the other embodiments of a sheath or other medical device which are described herein.

EXAMPLES

Example 1

Sheath Having a Pouch

A sheath having the design shown in FIGS. 10 and 11 is constructed having a top side (opposite the palm side) made from NEOPRENE polychloroprene which is between 1 and 4 millimeters thick. The interior of the sheath below the pouch is provided with a rubberized sticky lining to prevent the sheath from inadvertently sliding off a finger in the presence of perspiration or other water source.

The bottom side (palm side) of the sheath is formed from terry cloth, i.e. a cotton fabric with a moisture-absorbing loop pile covering, to provide optimal absorption of perspiration and an optimal gripping platform.

Example 2

Use of a Sheath Comprising Different Materials

A sheath is provided having a top surface and a bottom surface made from different materials. One surface comprises a material that is thicker and less flexible or elastic than the other surface to provide an individual with more (or less) support as desired.

An individual having an injury in a digit wears the foregoing sheath around the injured digit so that the thicker material is positioned on the palm side of the finger, creating a maximal flex resistance. Once the injury has subsided, the sheath is worn by the individual such that the thinner material is positioned on the palm side, thereby providing greater flexibility.

The foregoing description is merely illustrative and not limiting, having been presented by way of example only. Although examples have been shown and described, it will be apparent to those having ordinary skill in the art that changes, modifications, and/or alterations can be made. Throughout this description, the embodiments and examples shown should be considered as exemplars, rather than limitations on the apparatus and methods disclosed or claimed.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

This patent incorporates by reference U.S. Provisional Patent Application No. 60/743,674 filed Mar. 22, 2006, which discloses devices and features which can be combined with or complementary to those described herein.

What is claimed is:

1. A sheath for a finger, the sheath having an outer surface, a top side and a bottom side, comprising: a flexible cylindrical body shaped to fit around a joint of the finger; a pouch on the cylindrical body, the pouch being adjacent to the joint when the sheath is worn on the finger; and a thermal insert retained in the pouch, wherein the outer surface of at least the bottom side of the sheath comprises a frictional surface for gripping objects.

2. The sheath of claim 1, wherein the frictional surface comprises frictional elements, the frictional elements optionally being bumps, dots, or ridges.

3. The sheath of claim 2, wherein the frictional elements are arranged based on the surface of a basketball.

4. The sheath of claim 2, wherein the frictional elements are arranged based on the surface of a volleyball.

5. The sheath of claim 2, wherein the frictional elements are arranged based on the surface of a football.

6. The sheath of claim 1, wherein the thermal insert comprises a material which retains heat or cold.

7. The sheath of claim 1, wherein the thermal insert comprises a material which releases heat when activated.

8. The sheath of claim 7, wherein the material is a ferrous material adapted to oxidize and thereby generate heat.

9. The sheath of claim 1, wherein the insert comprises a material which releases cold when activated.

10. The sheath of claim 1, wherein the thermal insert provides additional rigidity to the sheath.

11. The sheath of claim 1, wherein the pouch comprises an opening, and wherein the thermal insert is sized to be placed through the opening and to be retained in the pouch.

12. The sheath of claim 11, wherein the opening is removably secured in a closed position by fasteners.

13. The sheath of claim 1, wherein the top side and the bottom side of the sheath are formed from different materials, and wherein the top side of the sheath is formed from an insulating material.

14. The sheath of claim 1, wherein the cylindrical body is formed from a polymer comprising an anti-bacterial agent.

15. The sheath of claim 1, wherein the cylindrical body is formed from a polymer comprising an anti-fungal agent.

16. The sheath of claim 1, wherein the pouch further comprises a topical ointment.

* * * * *